United States Patent [19]

Meek

[11] Plant 4,783

[45] Oct. 27, 1981

[54] CARNATION PLANT

[75] Inventor: Jack M. Meek, Salinas, Calif.

[73] Assignee: Yoder Brothers, Inc., Barberton, Ohio

[21] Appl. No.: 175,421

[22] Filed: Aug. 5, 1980

[51] Int. Cl.[3] ..... A01H 5/00
[52] U.S. Cl. ..... Plt./72
[58] Field of Search ..... Plt./72

*Primary Examiner*—James R. Feyrer
*Attorney, Agent, or Firm*—Schwartz, Jeffery, Schwaab, Mack, Blumenthal & Koch

[57] ABSTRACT

A carnation named Duchess, a spontaneous mutant of the cultivar Queen (disclosed in U.S. plant patent application, filed Oct. 31, 1979, Ser. No. 89729, now U.S. Plant Pat. No. 4,668). Duchess is particularly characterized by its commercial double flower type; flat flower form, twisting slightly with maturity; medium flower size; dark salmon pink flower color with minimum color oxidation; medium flowering response; 4 to 7 flowers and buds showing color per flowering stem; medium peduncle length; strong peduncle strength; and tall plant height.

1 Drawing Figure

The present invention comprises a new and distinct cultivar of *Dianthus caryophyllus, L.,* hereinafter referred to by the name Duchess.

Duchess is a spontaneous mutant of the cultivar Queen, disclosed in U.S. Plant patent application filed Oct. 31, 1979, Ser. No. 89,729. Duchess was discovered as one flowering plant within a flowering block of Queen by Jack M. Meek on May 15, 1980. Duchess was selected to expand the color range of the parental cultivar.

The first act of asexual reproduction of Duchess was accomplished when vegetative cuttings were taken from the initial selection in May 1980 in a controlled environment in Salinas, Calif. by a technician working under formulations established and supervised by Jack M. Meek.

Horticultural examination of selected units initiated May 15, 1980 has demonstrated that the combination of characteristics as herein disclosed for Duchess are firmly fixed and are retained through successive generations of asexual reproduction.

Duchess has not been observed under all possible environmental conditions. The phenotype may vary significantly with variations in environment such as temperature, light intensity, and daylength. The following observations, measurements, and comparisons describe plants grown in Salinas, Calif. under greenhouse conditions which approximate those generally used in commercial practice.

The following traits have been repeatedly observed and are determined to be basic characteristics of Duchess which in combination distinguish this carnation as a new and distinct cultivar:

(1) Commercial double flower type.

(2) Flat flower form, twisting slightly with maturity.

(3) Medium flower size, ranging from 45 to 60 mm. in diameter.

(4) Dark salmon pink flower color with smooth color oxidation.

(5) Medium flowering response.

(6) 4 to 7 flowers and buds showing color per flowering stem.

(7) Medium peduncle length, ranging from 10 to 12 cm.

(8) Strong peduncle strength.

(9) Tall plant height.

Of the several commercially available carnations known to the present inventors, the most similar in comparison to Duchess are Queen and Flamingo (unpatented). Reference is made to Chart A which compares selected characteristics of Duchess with those same characteristics of Queen and Flamingo. General comparisons are as follows:

(1) In comparison to Queen, Duchess has different flower color. All other characteristics of Duchess are similar to those same characteristics of Queen.

(2) In comparison to Flamingo, Duchess has smaller flower size, faster flowering response, longer peduncle length, and shorter plant height. The flower color, number of buds and flowers per stem, and peduncle strength of Duchess are similar to those same characteristics of Flamingo.

The accompanying photographic drawing is a color photograph showing typical inflorescence and foliage characteristics of Duchess. Colors are as nearly true as possible with illustrations of this type.

In the following description, color references are made to A Limit Color Cascade, by the Munsell Company, 1972 edition. Color values were determined between 8:30 A.M. and 9:00 A.M. on May 21, 1980 under 100 foot-candle light intensity at Salinas, Calif.

Classification:

*Botanical.*—*Dianthus caryophyllus, L.* "Duchess".

*Commercial.*—Spray carnation for cut flower production.

Inflorescence characteristics:

*Flowering response.*—Medium, ranging from 22 to 30 weeks.

*Inflorescence type.*—Semi-compound spray, with 1 to 4 buds per lateral, with reduced bud count during lower light periods; occasionally seen as a terminal spray, with 1 bud per lateral, especially on second cropping.

*Number of buds and flowers per stem.*—4 to 7 showing color on first crop.

*Peduncle length.*—Medium, ranging from 10 to 12 cm. on top flower.

*Flower.*—Size: Medium, 45 to 65 mm. in diameter when grown as a spray; too small for adaption as a commercial disbud. Type: Commercial double, petals from 20 to 25 in number. Form: Flat, twisting slightly with maturity.

*Corolla.*—Smooth texture, both abaxial and adaxial; deeply serrated petal margin.

*Corolla color.*—General Tonality from a distance of three meters: dark salmon pink 37-4 streaked over 37-3. Abaxial: 38-6 (immature) opening to 38-5 oxidizing rapidly to 38-5 streaked over 38-3. Adaxial: 38-4 streaked over 38-3.

*Keeping quality.*—On plant, up to 18 days; as a cut flower up to 15 days under room temperature of 20° C.

*Fragrance.*—Very slight to none, typical carnation.

*Reproductive organs.*—Androecium: Typical carnation, normal in all respects; long filament length, moderate to abundant pollen. Gynoecium: Typical carnation, normal in all respects; white pistil of medium length approximately 30 to 32 mm.

Plant characteristics:

*Growth and duration.*—Bushy and vigorous semi-erect perennial; typical of cultivars adaptable to commercial cut spray production.

*Branching pattern.*—Semi-erect, numerous and unrestricted at base of plant.

*Height.*—Tall, 80 to 85 cm. at time of first cut grown as a pinched plant.

*Stem.*—Strong, with bend of 5 to 10 degrees (Society of American Florist's Standards), almost brittle during low light periods; approximately 50 to 55 cm. in length from top to first vegetative lateral.

*Foliage.*—Occurrence: Abundant; typical carnation. Color (Abaxial): Approximately 21-14 to 21-15 but more greyed. Color (Adaxial): Approximately 21-14 but more greyed.

CHART A

COMPARISON OF DUCHESS, QUEEN AND FLAMINGO

| CULTIVAR | FLOWER COLOR | FLOWER SIZE | NO. OF BUDS & FLOWERS PER STEM | FLOWERING RESPONSE PERIOD |
|---|---|---|---|---|
| DUCHESS | dark salmon pink | 45 to 60 mm. | 4 to 7 | 22 to 30 weeks |
| QUEEN | light salmon pink | 45 to 60 mm. | 4 to 7 | 22 to 30 weeks |
| FLAMINGO | dark salmon pink | 60 to 85 mm. | 4 to 7 | 25 to 34 weeks |

| CULTIVAR | PEDUNCLE LENGTH | PEDUNCLE STRENGTH | PLANT HEIGHT |
|---|---|---|---|
| DUCHESS | medium 10 to 12 cm. | strong | tall 80 to 85 cm. |
| QUEEN | medium 10 to 12 cm. | strong | tall 80 to 85 cm. |
| FLAMINGO | short 5 to 8 cm. | strong | very tall 90 to 100 cm. |

COMPARISONS MADE OF PINCHED, FLOWERING PLANTS GROWN AS NATURAL SPRAYS IN SALINAS, CALIFORNIA

I claim:

1. A new and distinct cultivar of carnation known by the cultivar name Duchess, as described and illustrated, and particularly characterized as to uniqueness by the combined characteristics of commercial double flower type; flat flower form, twisting slightly with maturity; medium flower size, dark salmon pink flower color with minimum color oxidation; medium flowering response; 4 to 7 flowers and buds showing color per flowering stem; medium peduncle length; strong peduncle strength; and tall plant height.

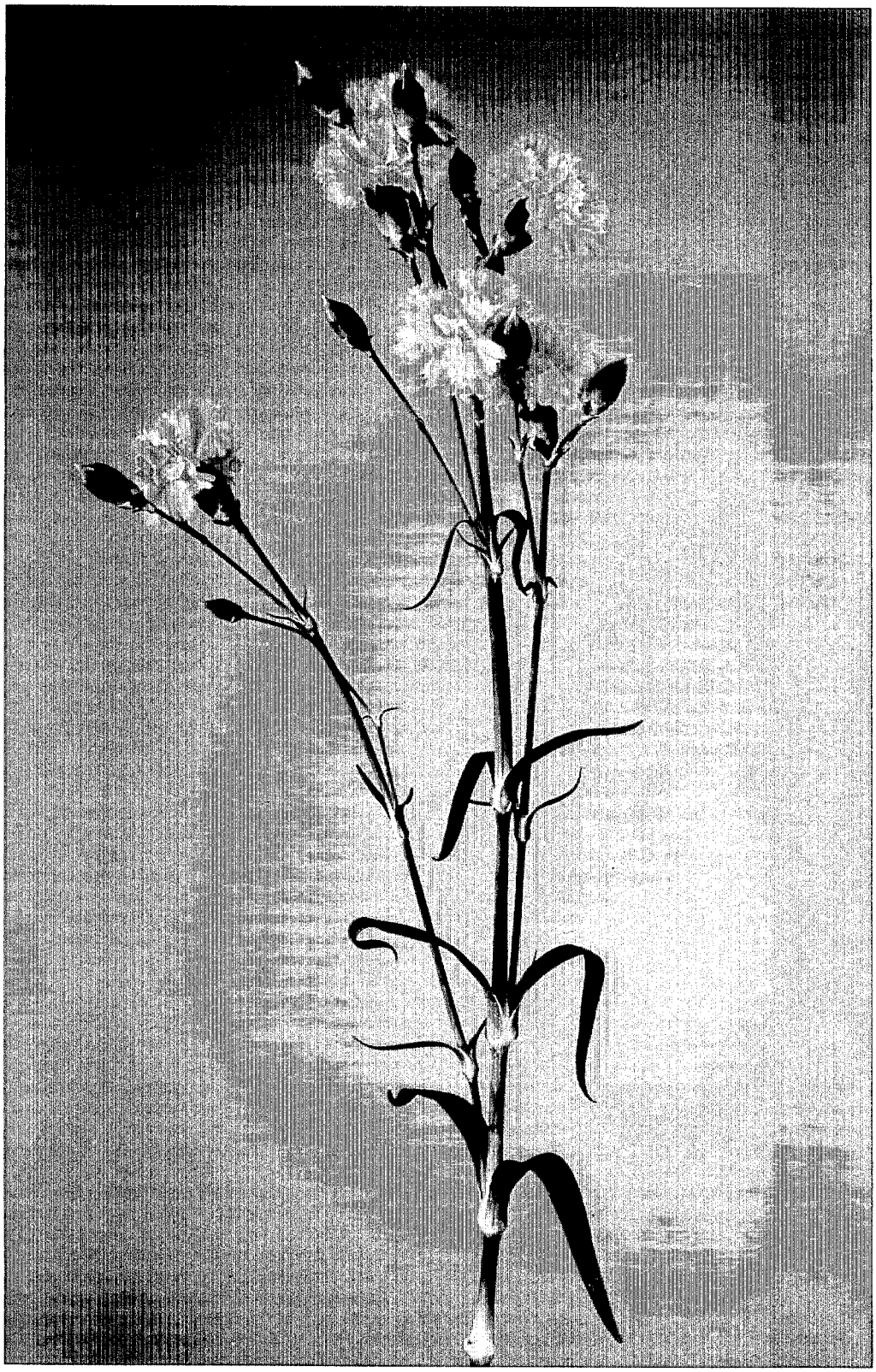

* * * * *